United States Patent [19]

Shoemaker

[11] Patent Number: 4,726,367
[45] Date of Patent: Feb. 23, 1988

[54] SURGICAL INSTRUMENT FOR IMPLANTING AN INTRAOCULAR LENS

[76] Inventor: David W. Shoemaker, 3026 Sailpoint Cir., Venice, Fla. 33595

[21] Appl. No.: 767,147

[22] Filed: Aug. 19, 1885

[51] Int. Cl.⁴ .............................................. A61B 17/00
[52] U.S. Cl. ................................. 128/303 R; 81/355
[58] Field of Search ................ 128/303 R, 321, 354, 128/346; 81/355; 294/1.2; 623/6

[56] References Cited

U.S. PATENT DOCUMENTS

| | | | |
|---|---|---|---|
| 984,756 | 2/1911 | Frisch | 128/321 |
| 1,518,021 | 12/1924 | Truxillo | 433/159 |
| 3,001,320 | 9/1961 | Sonner | 128/321 X |
| 3,613,683 | 10/1971 | Kees | 128/321 |
| 4,143,427 | 3/1979 | Anis | 128/321 X |
| 4,159,546 | 7/1979 | Shearing | 623/6 |
| 4,190,049 | 2/1980 | Hager et al. | 128/303 R |
| 4,198,980 | 4/1980 | Clark | 128/303 R |
| 4,214,585 | 7/1980 | Bailey | 128/303 R |
| 4,251,887 | 2/1981 | Anis | 128/303 R X |
| 4,258,716 | 3/1981 | Sutherland | 128/318 |
| 4,325,375 | 4/1982 | Nevyas | 128/321 |
| 4,326,306 | 4/1982 | Poler | 128/303 R X |
| 4,366,582 | 1/1983 | Faulkner | 623/6 |
| 4,403,354 | 9/1983 | Rainin | 623/6 |
| 4,435,855 | 3/1984 | Pannu | 128/774 X |
| 4,437,194 | 3/1984 | Hahs | 623/6 |
| 4,446,582 | 5/1984 | Hanna | 623/6 |
| 4,463,458 | 8/1984 | Seidner | 623/6 |
| 4,602,631 | 7/1986 | Funatsu | 128/321 |

FOREIGN PATENT DOCUMENTS 2852559 8/1980 Fed. Rep. of Germany ...... 128/346

OTHER PUBLICATIONS

Sparta, Opthalmic Instruments Brochure.

Primary Examiner—Michael H. Thaler
Attorney, Agent, or Firm—Fay, Sharpe, Beall, Fagan, Minnich & McKee

[57] ABSTRACT

A surgical instrument includes a handle section and a body section operably connected thereto. The body section preferably has a first member and a second member which is slidable in relation to the first member. A jaw section is secured to the body section and includes a first jaw and a second jaw which are adapted to grasp an associated object. The jaws are axially slidable with respect to each other from a predetermined minimum distance wherein the two jaws are not in contact with each other to a predetermined maximum distance. An intraocular lens, which can be inserted in an eye with the instrument includes a lens portion and two flexible haptic elements positioned on opposite sides of the lens portion and extending radially outwardly therefrom. Each element includes a memory retaining filament connected at both ends to a periphery of the lens portion to form a closed loop and define a continuous substantially circular arc having a diameter greater than the lens diameter. The arc is curved toward the lens portion and terminates in a free end spaced therefrom. A positioning aperture is provided in a positioning member located on the periphery of the lens to prevent the aperture from moving into the line of sight if the lens undergoes decentration. A method for using the instrument for implanting the lens is also disclosed.

28 Claims, 4 Drawing Figures

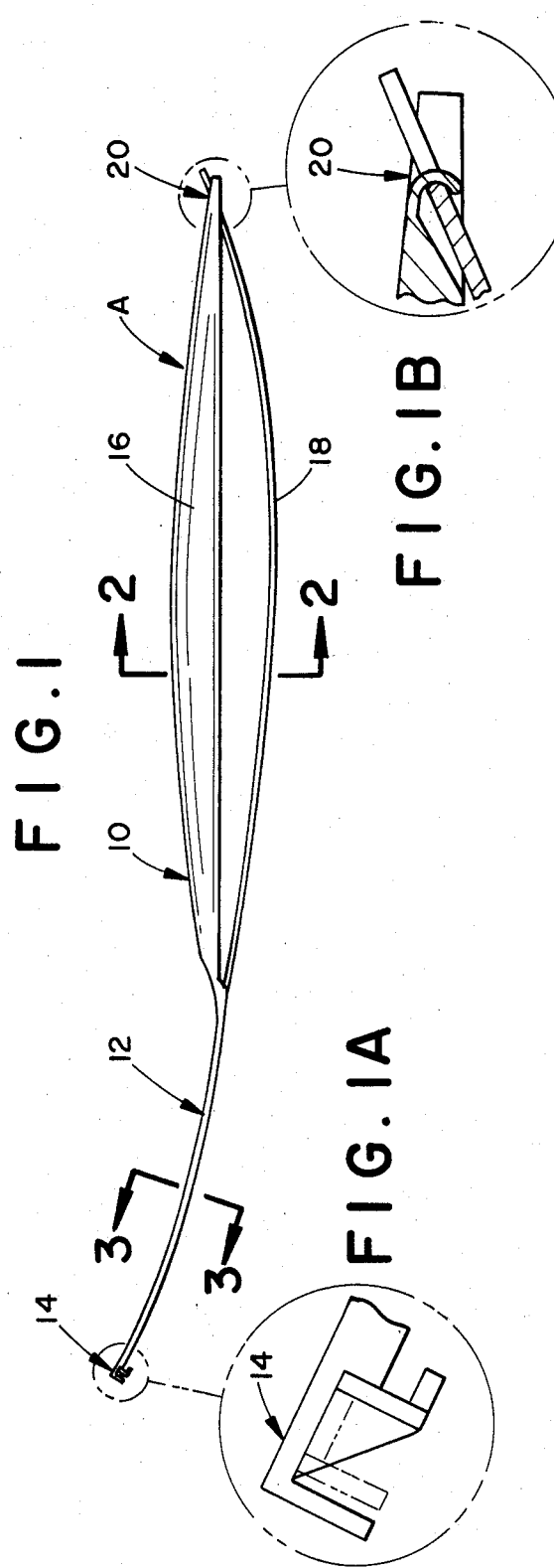
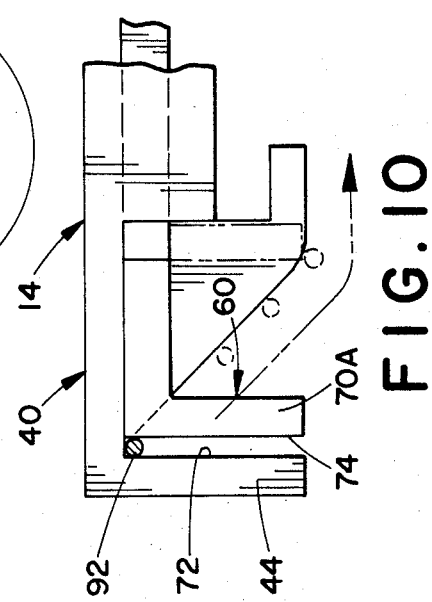
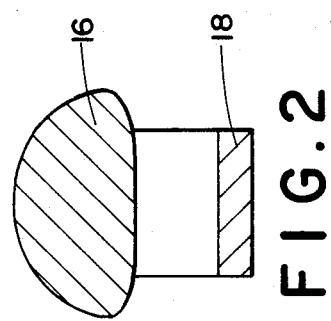
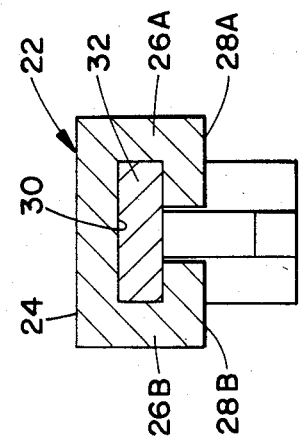

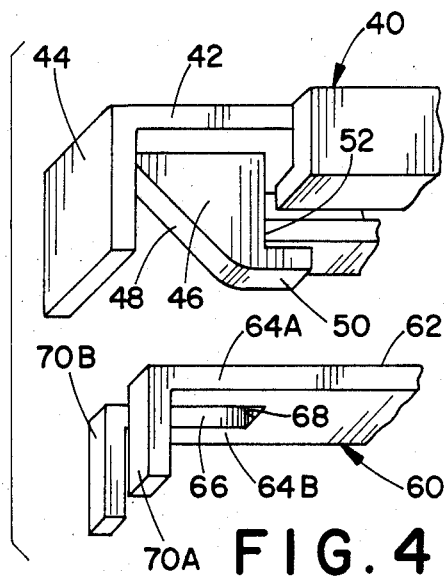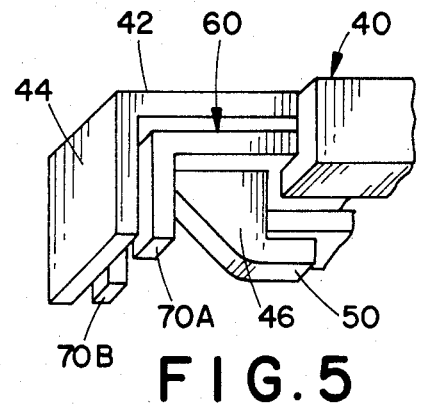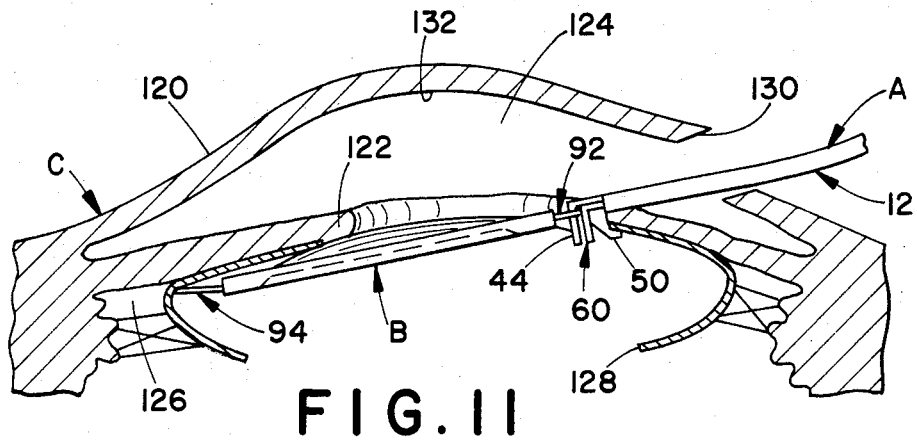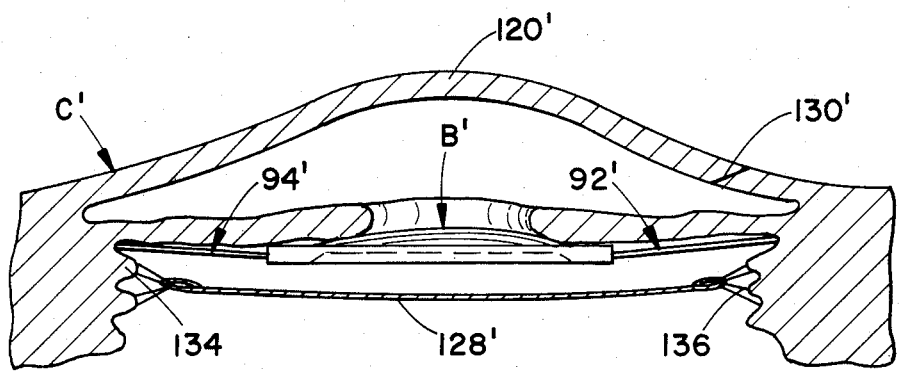

SURGICAL INSTRUMENT FOR IMPLANTING AN INTRAOCULAR LENS

BACKGROUND OF THE INVENTION

This invention generally pertains to hand manipulated instruments. More specifically, the present invention relates to a handle and jaws mechanism which can be adapted for use in a surgical instrument. The invention also relates to an intraocular lens and a method of using the instrument to implant the intraocular lens into the eye.

The invention is particularly applicable to a forceps-like instrument useful in cataract surgery, and will be described with particular relation thereto. However, it will be appreciated by those skilled in the art that the invention has broader applications and may also be adapted for use in many other hand manipulated instruments such as scissors and the like.

In the normal eye, light enters through the cornea, passes through the anterior chamber and pupil and is focused by the lens to form an image on the retina. The lens is surrounded by a capsule consisting of an anterior portion and a posterior portion. When the disease known as cataracts occurs, the lens becomes clouded or opaque. This interferes with transmission of light to the retina, and hence vision. The only known cure for cataracts is removal of the affected tissue. However, once the affected tissue has been removed from the eye, light entering the eye will not be properly focused on the retina without some artificial aid. Such aid can be provided by eyeglasses or by contact lenses; however, these aids do not provide satisfactory vision correction, comfort or convenience in most cases. Intraocular lenses, which are surgically implanted within the eye, have therefore become common as an alternative to eyeglasses and contact lenses.

As generally utilized in the ophthalmologic art, the term "intraocular lens" refers to an assembly including both a light focusing element or optic and haptics or support structures which serve to anchor the optic in place within the eye. Presently available intraocular lenses are commonly categorized as either "anterior chamber", "iris supported", or "posterior chamber".

The posterior chamber may be considered to be the most advantageous for intraocular lens implantation because the original lens was located in that chamber. However, it is also the most difficult and least accessible area for such implantation. Despite this, two types of posterior chamber lens implantation techniques have become common.

In an "extracapsular" procedure, only the nucleus and the anterior capsule of the eye are removed with the posterior capsule being left in place. Thus, the intraocular lens can be implanted "in the bag," i.e., the posterior capsule, or in front of the bag, in the sulcus.

Most conventional intraocular lenses need a special forceps-type instrument to grasp the lens during the process of positioning the lens in the eye. Such conventional forceps, however, do not preclude crushing damage to the haptic due to excessive handle compression by the surgeon. Existing intraocular lens forceps also do not have the capacity to allow for placement and release of the superior haptic (the lens support structure lying towards the patient's head) within the desired plane in a controlled and directional manner. To do so presently requires either a two-handed technique in which corneal, scleral or uveal tissue is directly manipulated with a second instrument or a torquing motion of the forceps and the intraocular lens during the release maneuver. Both of these are unnecessary and potentially hazardous.

In addition, no conventional forceps has the capacity for simultaneous iris retraction so that the anatomy in the eye can be seen by the surgeon during the lens implantation procedure. Therefore, both of the surgeon's hands are necessary and the surgeon must at times assume awkward hand positions.

Conventional posterior chamber lenses include the so-called "Shearing" lens which has two J-shaped resilient support members extending from its optic. The support members engage the wall of the eye or the ciliary sulcus immediately to the rear of the iris and effectively retain the optic against decentration (that is movement away from the center of the eye) or movement transversely of the axis of the eye. But, such conventional lenses do not have haptics which contact eye tissue over a wide area to maximize the distribution of haptic pressure and thus minimize tissue damage and to provide a stable intraocular support.

Accordingly, it has been considered desirable to develop a new and improved surgical instrument as well as a new and improved intraocular lens and method for implantation of the lens in the eye with the instrument which would overcome the foregoing difficulties and others while providing better and more advantageous overall results.

BRIEF SUMMARY OF THE INVENTION

In accordance with the present invention, a new and improved surgical instrument is provided for manipulating an object.

More particularly in accordance with the invention, the instrument includes a handle means for holding the instrument as well as actuating means for manually actuating the instrument. A body section is provided which is operably connected to the handle means and a jaw section is operably connected to the body section. The jaw section includes a first jaw and a second jaw which are adapted to grasp and manipulate an associated object. The first and second jaws are slidable with respect to each other from a predetermined minimum distance wherein the two jaws do not contact each other to a predetermined maximum distance upon a manipulation of the two handle members.

According to another aspect of the invention, the first jaw includes a head portion, and an arm portion extending approximately transversely to the head portion. The instrument further includes a flange extending approximately transversely to both the head portion and the arm. The flange is positioned adjacent the arm. Preferably, the invention further includes a hook portion which is positioned on a free end of the flange. The hook is adapted to contact the iris or the capsular flap of an eye during use of the instrument to insert an associated intraocular lens into the eye.

According to still another aspect of the invention, a centering strand of an associated intraocular lens is released in controlled directional manner by being slid along the flange as the second jaw is retracted from the first jaw.

According to yet another aspect of the invention, the second jaw includes a head portion, a pair of spaced apart arms, and a pair of spaced apart fingers, one extending approximately transversely from each of the arms.

According to yet still another aspect of the invention, the handle means includes first and second elongated handle members with the second handle member being resiliently urged into a first position in which the first and second jaws are at the predetermined maximum distance.

According to a further aspect of the invention, the first and second handle members are connected by a ducktail hinge located at one end of the handle members.

According to a yet further aspect of the invention, the body section includes a first body member and a second body member which is substantially encircled by the first body member. Preferably, the first jaw is integral with the first body member and the second jaw is integral with the second body member.

According to a still yet further aspect of the invention, the first jaw arm and the second jaw fingers are substantially parallel to each other.

According to still yet a further aspect of the invention, the instrument is made of strong and lightweight metal. Preferably, the metal is a titanium alloy.

In accordance with another aspect of the invention, an intraocular lens, which may be implanted with the instrument, is provided.

More particularly, in accordance with this aspect of the invention, the lens includes a lens body and first and second flexible haptic elements positioned on opposite edges of the lens body and extending radially outwardly therefrom. Each such haptic element includes a memory retaining filament connected at both ends to a periphery of the lens body to form a closed loop. Each haptic extends away from the lens body in a crescent-shaped arc having a diameter greater than the diameter of the lens body, with the arc being curved toward the lens body. Positioning means are provided on the lens periphery for enabling the lens to be positioned in an eye. The positioning means includes at least two positioning apertures which are located outside the diameter of the lens portion to prevent the apertures from moving into the line of sight if the lens undergoes decentration.

In accordance with still another aspect of the invention, the two haptic elements are positioned at an angle of approximately 5° to a plane of the lens to enable the haptic elements to be precisely directed into the desired plane of the eye.

In accordance with yet another aspect of the invention, each haptic element has an outer loop member which closely contacts eye tissue over a wide area to maximize distribution of haptic element pressure and thus minimize tissue damage. Such an area of haptic fixation can be at least 30° in arc to provide a stable intraocular support and to evenly distribute the pressure.

In accordance with still yet another aspect of the invention, the haptic element ends remote from the lens are provided with a notch area through which the lens can be manipulated by an associated lens forceps.

In accordance with yet still another aspect of the invention, the positioning means can include opposing flanges which extend from the periphery of the lens portion.

In accordance with yet still a further aspect of the invention, the positioning means can include a ring member which surrounds the lens portion outer periphery and holds the lens.

Still yet a further aspect of the invention relates to a method for implanting an intraocular lens in an eye.

According to this aspect of the invention, a biologically inert intraocular lens having a pair of centering strands is provided such that the centering strands extend from opposed peripheral edges of the lens. Also provided is a lens forceps having a handle section, and a body section connected to the handle section. The body section includes a pair of integral jaw members which are angled with respect to the body section and which are axially slidable with respect to each other. A first centering strand of the lens and the optic or lens are inserted through an incision in the eye in such a manner that a second centering strand of the lens is readied for placement. The second centering strand is then grasped with the forceps, passed through the incision and released in a controlled directional manner as one of the jaws is retracted from the other of the jaws.

An advantage of the present invention is the provision of a new hand manipulated instrument designed to be operated with one hand.

Another advantage of the invention is the provision of a surgical instrument which has the capacity to allow for placement and release of a superior haptic of an associated intraocular lens within the desired plane of the eye in a controlled and directional manner.

Still another advantage of the invention is the provision of an instrument which has the capacity for simultaneous partial iris or capsular flap retraction so that the relevant anatomy of the eye can be visualized during the critical point of the intraocular lens implantation procedure.

Yet another advantage of the invention is the provision of an instrument in which the instrument body portion is curved with respect to the plane of the instrument handle portion so that the surgeon does not have to assume awkward or less than optimal hand positions during the implantation procedure.

Still yet another advantage of the invention is the provision of an instrument which prevents crushing damage to the parts of the implanted lens engaged by the instrument jaws.

A further advantage of the invention is the provision of a new intraocular lens which is stably supported in the eye while simultaneously widely distributing the pressure exerted by the lens haptics on adjacent eye tissue.

A still further advantage of the invention is the provision of an intraocular lens in which haptic angulation is reduced to 5° in order to eliminate the occassional difficulty of precisely directing an inferior haptic into the desired plane of the eye without increasing the possibility of pupillary capture or significant iris contact.

A yet further advantage of the invention is the provision of an intraocular lens in which the optic is supported by a uniplanar carrier ring which allows application of many of the currently available intraocular lens forceps directly to the carrier ring and avoids the possibility of scoring the optic by providing positioning apertures only on the ring.

A still yet further advantage of the present invention is the provision of an intraocular lens which has four point optic fixation to minimize the tendency for intraocular lens torsion and decentration. Thus, the intraocular lens of the present invention remains well centered within the frontal plane during and subsequent to implantation.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts, preferred and alternate embodiments of which will be described in detail in this specification and illustrated in the accompanying drawings which form a part hereof, and wherein:

FIG. 1 is a side elevational view of a surgical instrument according to the present invention;

FIG. 1A is an enlarged side elevational view of a jaw portion of the instrument of FIG. 1;

FIG. 1B is an enlarged side elevational view in partial cross section of a tail portion of the instrument of FIG. 1;

FIG. 2 is an enlarged cross-sectional view along line 2—2 of the instrument of FIG. 1;

FIG. 3 is an enlarged cross-sectional view along line 3—3 of the instrument of FIG. 1;

FIG. 4 is an enlarged exploded perspective view of a jaw portion of the instrument of FIG. 1;

FIG. 5 is a perspective view of the jaw portion of FIG. 4 in an assembled condition;

FIG. 10 is an enlarged side elevational view of the jaw portion of the instrument of FIG. 1 holding a haptic element of the lens according to FIG. 6;

FIG. 11 is a schematic view of a human eye showing the instrument of FIG. 1 installing the lens of FIG. 6 in the eye; and, FIG. 12 is a schematic view of a human eye with the intraocular lens of FIG. 6 shown in an installed position in the eye.

DETAILED DESCRIPTION OF THE PREFERRED AND ALTERNATE EMBODIMENTS

Figure 6:
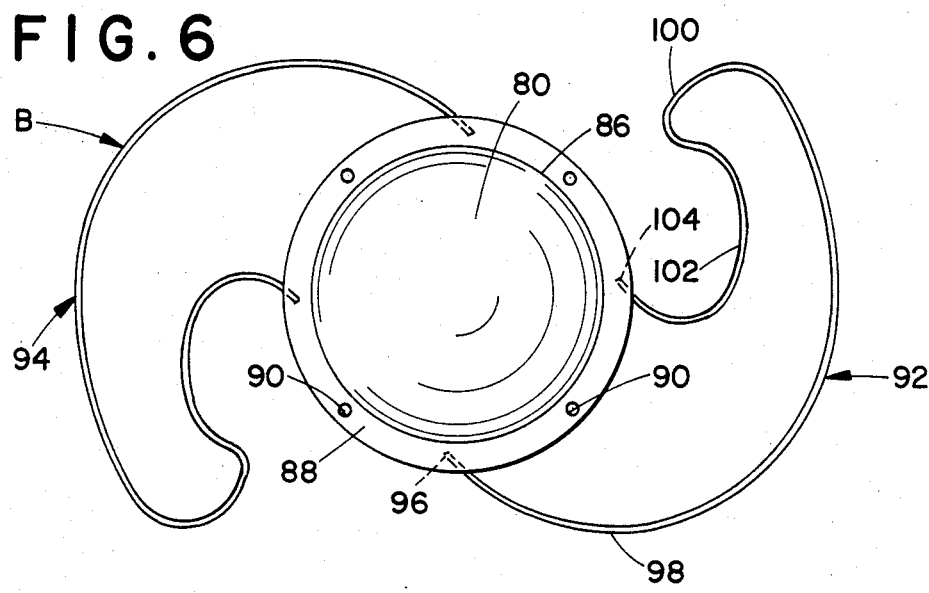
FIG. 6 is a top plan view of an intraocular lens according to the present invention.

Referring now to the drawings wherein the showings are for purposes of illustrating preferred and alternate embodiments of the invention only and not for purposes of limiting same, FIG. 1 shows the subject invention as a surgical instrument while FIG. 6 illustrates a preferred intraocular lens which can be manipulated with the instrument. While the instrument is primarily designed for and will hereinafter be described in connection with the installation of the intraocular lens according to FIG. 6, it will be appreciated that the instrument can be used in the installation of other intraocular lenses and can also be adapted for use in other surgical environments. Moreover, the invention may also be adapted for use in other types of hand manipulated instruments such as scissors or the like.

More particularly, and with reference to FIG. 1, the instrument may be termed a lens forceps A which includes a handle means or structure 10, a body structure 12, and a jaw structure 14 which is enlarged in FIG. 1A for clarity. The handle structure 10 preferably includes a first handle 16 as well as a second handle 18 and a ducktail hinge 20 which connects the two handles at one end as shown in FIG. 1B. Of course, any other conventional way of connecting the two handles could also be utilized.

With reference also to FIG. 2, the first handle 16 can be oval-shaped and can have a substantial thickness at its middle section, while the second handle 18 is preferably planar and thin in comparison to the width of the first handle. The ducktail hinge 20, in conjunction with the handle shapes, is useful since it provides a means for resiliently urging the instrument into one configuration or position. Also, the planar second handle 18 provides a means for actuating the instrument when the second handle is squeezed toward the first handle 16 as will be described further hereinbelow.

With reference now also to FIG. 3, the body structure 12 can include a first body portion 22 having a top wall 24, a pair of sidewalls 26A, 26B and a pair of bottom flanges 28A, 28B which extend approximately transversely to the sidewalls and inwardly toward each other so that the wall members define a bore 30 in the first body portion 22. A flat second body portion 32 is disposed in a slidable manner within the bore 30. It should be recognized, of course, that other configurations of the first and second body portions 22, 32 could be provided such as a tubular first body portion and a rod-like second body portion. It is important only that the body portions be slidable with respect to each other and that they maintain the jaw components in proper relation to each other.

Preferably, the body structure 12 curves upwardly from the longitudinal plane of the first handle portion 16 in a continuous curve which can range from 0° to 20°. This allows the surgeon to assume comfortable hand positions throughout the use of the instrument.

With reference now to FIGS. 1A, 4 and 5, the jaw structure 14 includes a first jaw 40 having a head portion 42, and an arm 44 extending approximately transversely thereto. A flange 46 extends approximately transversely to both the head 42 and the arm 44 and is preferably located on the head adjacent the arm. Preferably, the flange 46 includes an angled surface 48 which leads away from the arm 44, a hook portion 50 disposed at the free end of the angled surface 48, as well as a flat back surface 52. The angled surface serves to control the movement of a strand of an intraocular lens so that it is released in a controlled directional manner as will be further explained hereinbelow. The hook portion 50 serves to engage and move a section of the iris or capsule of the eye when the forceps is used to install an intraocular lens in an eye as shown in FIG. 11.

The second jaw member 60 includes a body portion 62 as well as a pair of arms 64A, 64B extending therefrom and defining between them a gap 66 having a flat back wall 68. A pair of fingers 70A, 70B extend approximately transversely, one from each of the arms 64A, 64B. The haptic of an associated intraocular lens is grasped between the two jaws 40, 60 but will not be crushed therebetween even if a strong pressure is exerted by the jaws since the second jaw flat back wall 68 will contact the flange back surface 52 and prevent any further movement of the second jaw toward the first jaw.

It should be recognized, of course, that other jaw configurations could also be employed, it being only important that they perform at least one of the following three functions, and ideally all three: (1) prevent a crushing damage to the haptic of an associated intraocular lens; (2) provide a means for releasing the haptic in a controlled directional manner; and (3) provide a means for retracting a portion of the iris or capsular flap during the implantation of the lens. For example, two side flanges could be provided on the first jaw with a central second jaw finger portion extending between them instead of a central flange with a finger on either side thereof. Also, the first jaw arm 44 and the second jaw fingers 64A, 64B are preferably substantially parallel to each other but they do not necessarily have to be and could have other configurations.

Preferably, the instrument A is made out of a strong light-weight material, such as a titanium alloy. Of course, other metals or plastics could also be employed to construct the instrument.

The instrument A can be between approximately 10 and 30 cm. in length with the handle portion being from 21 to 27 cm. and the body portion being from 3 to 9 cm. in length, respectively. The handle portion can be approximately 6 to 18 mm. in width with the jaw portion being considerably narrower and on the order of approximately 1 to 3 mm. in width. In other words, the first jaw member 40 can be approximately 1 to 3 mm. in width with the second jaw member 60, which slides with respect to the first jaw member, being approximately 0.7 to 2.1 mm. in width. The minimum gap between the first jaw arm 44 and the second jaw fingers 70A, 70B can be on the order of 0.15 to 0.45 mm. to prevent crushing damage to the haptics to an intraocular lens. The second jaw fingers 70A, 70B can be on the order of 0.2 to 0.6 mm. in width each thus defining between them a gap of approximately 0.3 to 0.9 mm. The flange 46 which lies between fingers 70A, 70B can be approximately 0.2 to 0.6 mm. in width. Of course the instrument can also be made larger or smaller as desired for a particular application.

As mentioned the instrument A of the present invention is particularly adapted to grasp a strand or haptic of an intraocular lens during the process of implanting the lens in the eye. In one preferred embodiment and with reference now to FIGS. 6 and 7, an intraocular lens assembly B, according to the present invention includes a lens body 80 having a front optical surface 82 and a rear optical surface 84. An outer periphery 86 of the lens body 80 is surrounded by a ring 88 to support the lens body and also to provide additional fixation area in the eye. In this embodiment of the lens assembly, the ring 88 is a separate member which can be made of a biologically inert material, such as silicone, or plastic.

A plurality of positioning holes 90 are provided in the ring to allow the application of many of the currently available intraocular lens manipulating devices in positioning the lens assembly B in the eye. Preferably, four positioning holes 90 are provided at equally spaced intervals around the ring 88 although it should be recognized that any other suitable conventional number of positioning apertures could also be provided. The lens assembly B is also provided with a pair identically shaped haptic elements 92, 94. Since the haptic elements are identical, only the first haptic element 92 will be described, it being recognized that the second haptic element has the identical structure.

The first haptic element 92 is provided with a first end 96 which is secured to the ring 88 and has a first strand portion 98 extending outwardly therefrom. A notch portion 100 is positioned at the end of the first strand portion 98 and connects to a second strand portion 102 which leads back toward the ring 88 and terminates in a second end 104 attached to the ring.

Thus, each haptic element 92, 94 defines a continuous substantially circular arc having a diameter greater than the diameter of the lens portion with the arc being curved toward the lens portion and terminating in a free end, which is where the notch 100 is located, spaced from the lens body 80. In this way, the two haptic elements 92, 94 form crescent-shaped arcs having a diameter greater than the diameter of the lens body 80. The haptic first strand portion 98 is adapted to contact eye tissue over a wide area to minimize eye tissue damage and also maximize support of the lens assembly A in the eye. To this end, the haptics 92, 94 are adapted to contact eye tissue over approximately 30° of arc each.

The haptic elements 92, 94 are preferably made in the form of a memory retaining filament or strand. They can be made from any biologically inert and structurally suitable filament or strand material, such as plastics, for example, polypropylene, polyamide or polymethylmethacrylate. The haptic elements can, for example, be anywhere from 0.14 to 0.21 millimeters in diameter.

Figure 7:
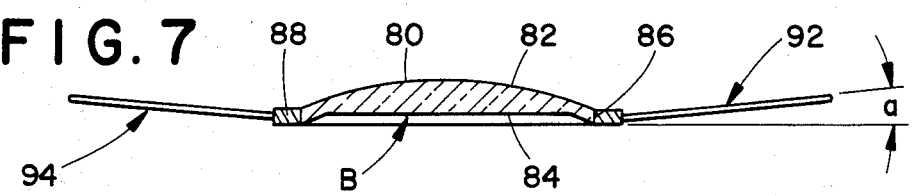
FIG. 7 is a side elevational view of the intraocular lens of FIG. 6.

The lens body 80 can be made from any material having suitable optical, structural, and biological properties. Polymethylmethacrylate is one suitable material for the lens body. In one preferred embodiment, the lens body can be approximately 6.0 millimeters in diameter with the thickness of the optic and the precise shape of its anterior surface being selected to provide the appropriate refractive effect for the particular eye in which the lens will be implanted. In this connection, it can be seen that FIG. 7 illustrates a convex-planar type lens.

The ring 88 can also be made from any suitable conventional material, such as a plastic, for example, polymethylmethacrylate, or polypropylene. Since the strands 92, 94 can be made of the same material as the ring, the ring and strands can form a unitary member which can be conveniently produced in a single molding operation. Alternatively, the haptics or strands 92, 94 can be separately formed and welded, glued or otherwise adhered to the ring 88. If the ring material is somewhat flexible, the more rigid lens body 80 may be conveniently snapped into a ring 88 during assembly. The ring 88 may be approximately 0.5 mm. in width with the positioning holes being 0.25 mm. in diameter. The haptics 92, 94 can extend approximately 3.4 mm. away from the ring. Thus, the entire lens assembly B can have a maximum width of approximately 13.8 mm.

It should be noted that the haptic angulation of the lens B of the present invention is reduced to approximately 5° in order to eliminate the occassional difficulty of precisely directing the inferior haptic into the desired plane. In other words, the two haptic elements 92, 94 are located or angled at approximately a 5° angle a to the plane of the lenses as is evident from FIG. 7. This reduction of the angles of the haptics is accomplished without increasing the possibility of pupillary capture or significant iris contact due to the design of the lens assembly B. An ultraviolet filter may also be provided in the lens if that is thought desirable.

Figure 8:
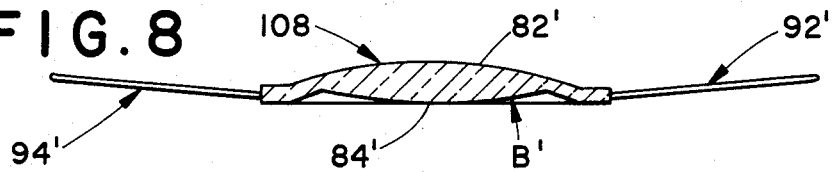
FIG. 8 is a side elevational view of an alternate embodiment of the intraocular lens according to the present invention.

With reference now to the alternate embodiment of FIG. 8, the invention is there illustrated as a convex-concave type lens with an integral lens-ring body. For ease of illustration and appreciation of this alternative, like components are identified by like numerals with a primed (') suffix and new components are identified by new numerals.

In this FIGURE, a lens assembly B' includes an integral lens and ring structure 108. The lens portion of this assembly has a curved rear optical surface 84' as well as a curved front optical surface 82'. It is evident that the combined ring and lens structure 108 can be made from a suitable transparent plastic, such as polymethylmethacrylate, or a like material. In this embodiment, the haptics 92', 94' can be formed integral with the lens structure 108 or can be separately secured thereto.

Figure 9:
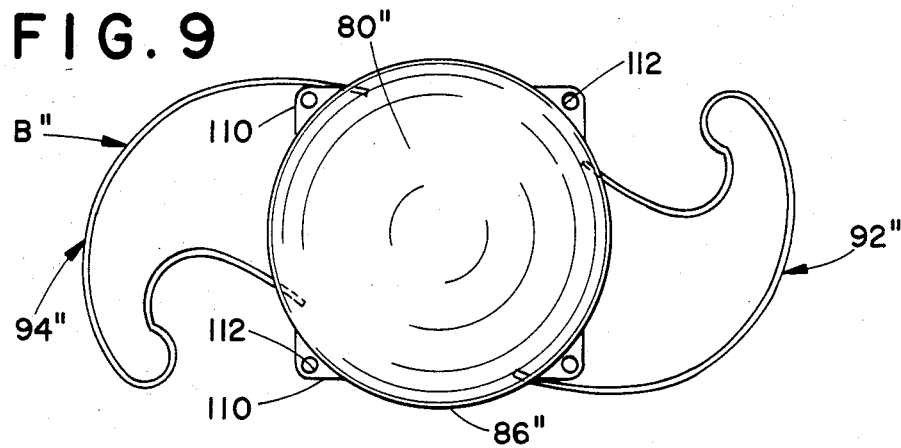
FIG. 9 is a top plan view of another alternate embodiment of an intraocular lens according to the present invention.

With reference now to the alternate embodiment of FIG. 9, another type of intraocular lens B" is shown there. For ease of illustration and appreciation of this alternative, like components are identified by like numerals with a double primed (") suffix and new components are identified by new numerals.

In this FIGURE, the intraocular lens B" is provided with a lens body 80" along with a pair of haptic positioning elements 92" and 94". In this case, however, the haptic elements are secured directly to the lens element and additional positioning protrusions or flanges 110 are located around the outer circumference or periphery 86" of the lens body. These protrusions 110 each contain a positioning hole 112. In both the preferred embodiment, which has a ring 88, and in the second alternate embodiment, which has positioning flanges 110, the positioning holes 90, 112 are moved radially outwardly away from the lens body. This is done so that if the lens decenters in the eye, the optic positioning holes do not get into the line of sight of the individual wearing the lens. Obviously, when such positioning holes do get into the line of sight, the lens becomes useless. By moving the positioning holes radially outwardly and locating them outside the diameter of the lens, the entire lens is made useful out to its diameter. In other words, the useful size of the lens is not restricted to a diameter smaller than its full diameter by locating optical positioning holes on the usable surface of the lens.

With reference briefly to FIG. 10, the first jaw arm 44 has a contact surface 72 which cooperates with a contact surface 74 provided on the second jaw fingers 70A, 70B to grasp a positioning strand or haptic 92 of an associated intraocular lens during the process of implanting the lens in the eye. The haptic element 92 which is grasped will be known as the superior haptic, with the other one being known as the inferior haptic. The inferior haptic is the one which is located toward the feet of the patient during the implantation procedure with the superior haptic being one located toward the head of the patient.

With reference now to FIG. 11, the lens forceps A of the present invention can be used to insert the lens assembly B into an eye C. In this connection, an outer loop or first strand portion 98 of one of the haptic elements 92, 94 can be grasped by the jaws 40, 60 of the forceps A.

In order to understand the surgical process, the structure of the eye will be briefly reviewed. With reference now to FIG. 11, a human eye includes a cornea 120, and an iris 122 positioned within the eye to form an anterior chamber 124. Behind the iris is a posterior chamber 126. Generally, posterior chamber lenses use an excavated lens sac posterior portion 128 to fix the lens B within the eye. Accordingly, such lenses require the use of an extracapsular surgical technique which leaves the posterior portion of the lens sac intact.

It must be appreciated that the surgical implantation of an intraocular lens is an extremely delicate procedure involving substantial surgical skill and dexterity. This is so because the intraocular lens and the attendant haptics are fairly large and in order for the surgeon to grip the lens with a surgical instrument and retain any degree of control requires extreme care during the insertion of the intraocular lens in the eye.

For such insertion, an incision 130 is made into or about the cornea 120 and the lens sac anterior portion is removed along with the cataracted lens. Subsequently, the lens B can be positioned in the eye C. As the haptics 92, 94 are positioned in the posterior chamber 126, any inadvertent movement of the surgeon's hand or a repositioning of the forceps must be prevented since that may result in the outer surface of the lens body contacting the inner surface or endothelium 132 of the cornea. If such contact occurs, the cornea may become foggy and the implantation of the intraocular lens will not result in satisfactory vision for the patient. Unfortunately, as the haptics are deformed to position the intraocular lens B in the eye C, the likelihood increases that the lens body will shift or twist and contact the endothelium 132 or otherwise be improperly positioned.

The forceps A of the present invention, however, prevent such problems by providing a one handed controlled directional haptic release with simultaneous iris retraction as well as a variably curved arm. The lens B, after a haptic thereof is grasped between the jaws of the forceps A, is inserted in the eye through the incision 130 in the cornea 120. The inferior haptic 94 is then compressed in the sac portion 128 by the insertion of the lens. This compression or bending of the haptic continues until the lens abuts the haptic and then a bending of the superior haptic 92 takes place because of the continued movement of the forceps into the eye.

The forceps hook portion 50 then hooks the iris 122 and/or the sac portion 128, also known as a capsular flap, to enable the surgeon to better see into the relevant anatomy of the eye during this most critical phase of the eye surgery. As mentioned, the curvature of the forceps body portion 12 in relation to the plane of the first handle enables the surgeon to maintain a comfortable hand position throughout the surgical process as the intraocular lens B is manipulated.

The superior haptic 92 is then released in a controlled directional manner, as shown in FIG. 10, since the haptic will slide up the angled surface 48 and past the hook 50 on the flange 46 and become successfully positioned in the sac portion 128. After the superior haptic 92 is released, it will return or snap back to its substantially nonstressed condition and become correctly positioned in the sac. At that point, the iris or capsular flap can be unhooked and the forceps A withdrawn.

One particular advantage of the forceps of the present invention is that it can enable lens implantation to take place with only one hand. Thus, both a left handed and a right handed surgeon can utilize the instrument for a lens implantation which is substantially one handed.

It should be noted, however, that the intraocular lens of the present invention can also be implanted out of the bag, as shown in FIG. 12, if the posterior portion of the bag or sac cannot be left intact. For ease of illustration and appreciation of this alternative, like elements are identified by like numerals with a primed (') suffix and other elements are identified by new numerals.

In this FIGURE, a lens B' has been inserted in a rear chamber 126' of the eye C'. An incision 130' of the cornea 120' of the eye has been closed. The two haptics 92', 94' of the lens B' contact the ciliary sulcus 134 of the eye. Behind the lens B', the shell of the bag 128' remains attached to the zonules 136. Implanted out of the bag, the haptics of the present invention, due to their wide area of stable intraocular lens support, will be prevented from migrating into major arterial vessels. Also the specter of late pressure necrosis will be prevented.

If, on the other hand, the intraocular lens is implanted in the bag, as shown in FIG. 11, the more even circumferential distribution of tissue pressure may also reduce the tendency for corrugation of the posterior capsule parallel to the axis of fixation. With the reduction of posterior capsule corrugation, and is attendant Maddox rod effect, an earlier visual rehabilitation may occur and fewer indications for YAG (yttrium aluminum garnet) laser capsulotomy will be seen. Such capsulotomy uses the laser's light to dissolve cloudy tissues which form on the surface of the posterior capsule.

The lens assembly B, since it preferably includes a carrier ring 88, which provides additional fixation in the eye, stabilizes the intraocular environment. Thus pseudophakodonesis is minimized and, more importantly, the visual axis is effectively sealed off to prevent vitreous prolapse into the anterior chamber following inadvertent rupture of the hyaloid face during or subsequent to YAG laser capsulotomy. Preferably, the lens assembly provides a four point equidistant optic fixation to minimize the tendency for intraocular lens torsion and decentration which may occur during or subsequent to lens implantation.

It should be noted that the lens assemblies B, B', and B" of the present invention can be installed not only by the lens forceps A disclosed herewith, but also by conventional types of forceps such as the well-known McPherson forceps. Also, the forceps A of the present invention can be used to install not only the lens assemblies of the present invention but also most conventional intraocular lenses having centering strands.

The subject invention thus relates to a hand manipulated instrument which can be used during eye surgery to implant intraocular lenses. The instrument provides for a controlled directional release of a haptic of an associated intraocular lens with simultaneous iris retraction. The instrument according to the present invention also has a variably curved arm so that the eye surgeon does not have to assume awkward or less than optimal hand positions during surgery. Moreover, the instrument also provides a stop mechanism which prevents the two jaws of the forceps from contacting each other thereby preventing a crushing damage to the haptic element or strand which is adapted to be grasped by the jaws.

The present invention also discloses an intraocular lens which is adapted to be installed in an eye by the instrument. The intraocular lens has a broad area of haptic fixation to provide stable intraocular lens support while maximizing the distribution of tissue pressure by the haptic elements. The lens according to the present invention also reduces haptic angulation to enable the haptics to be precisely directed into the desired plane in the eye. Also, the lens positioning holes are moved away from the lens body so that the entire diameter of the lens body becomes usable for sight and the lens can continue to be used by the wearer even if it undergoes decentration.

The present invention further discloses a method for implanting an intraocular lens in the eye through the use of the instrument.

The invention has been described with reference to preferred and alternate embodiments. Obviously, modifications and alterations will occur to others upon the reading and understanding of this specification. It is intended to include all such modifications and alterations insofar as they come within the scope of the appended claims or the eqivalents thereof.

Having thus described the invention, it is now claimed:

1. An instrument for manipulating objects comprising:
   a handle means for holding the instrument, including actuating means for manually actuating the instrument;
   a body section operably connected to said handle means; and,
   a jaw section operably connected to said body section and including;
   a first jaw having a head portion and an arm portion extending approximately transversely to said head portion,
   a second jaw, said first and second jaws being adapted to grasp and manipulate an associated object, said first and second jaws being axially slidable with respect to each other from a predetermined minimum distance, wherein said two jaws do not contact each other, to a predetermined maximum distance upon a manipulation of said two handle members, and
   a guide means for guiding an associated object in a controlled directional manner away from said first jaw head portion and arm position as one of said first and second jaws is retracted from the other of said first and second jaws, said guide means extending approximately transversely to both said first jaw head portion and arm portion.

2. The instrument of claim 1 wherein said guide means comprises a planar flange which is substantially triangular in a side elevational view and wherein said flange is positioned near said arm.

3. The instrument of claim 2 wherein the instrument further includes a hook portion positioned on a free end of said flange, said hook portion being adapted to partially retract the iris or capsular flap of an eye during use of the instrument to insert an associated intraocular lens into said eye.

4. The instrument of claim 2 wherein said second jaw includes:
   a head portion;
   a pair of spaced apart arms; and,
   a pair of spaced apart fingers, one extending approximately transversely from each of said arms.

5. The instrument of claim 4 wherein said first jaw arm and said second jaw fingers are substantially parallel to each other and wherein said flange is secured to said first jaw head portion and is positioned between said second jaw arms.

6. The instrument of claim 4 wherein a sliding face is provided on a sloping surface of said flange, said sliding face leading away from said first jaw head portion and said first jaw arm porion, and wherein one of said second jaw spaced apart arms is positioned on either side of said flange.

7. The instrument of claim 1 wherein said handle means includes first and second elongated handle members with said second handle being resiliently urged into a first position in which said first and second jaws are at said predetermined maximum distance.

8. The instrument of claim 7 wherein said first and second handle members are connected by a ducktail hinge located at one end of said handle members.

9. The instrument of claim 1 wherein said actuating means includes a pair of handle members which are resiliently biased away from each other such that the instrument is actuated by squeezing said two handle members toward each other.

10. The instrument of claim 1 wherein said body section includes:
a first body member; and,
a second body member which is substantially encircled by said first body member.

11. The instrument of claim 10 wherein said first jaw is integral with said first body member and said second jaw is integral with said second body member.

12. The instrument of claim 10 wherein said first and second body members are curved with respect to a longitudinal plane extending through said handle means.

13. The instrument of claim 1 wherein the instrument is made of a strong and lightweight metal.

14. A forceps for manipulating objects, comprising:
a pair of handles which are hingedly connected;
a first body portion integral with a first of said handles, said first body portion being elongated and substantially tubular and being formed at its free end as a first jaw of the forceps, wherein said first jaw includes:
a head portion; and,
an arm at a free end of said head portion;
a second body portion integral with a second of said handles, said second body portion extending within said substantially tubular first body portion and being formed at its free end as a second jaw of the forceps, said first and second jaws being longitudinally slidable with respect to each other from a predetermined minimum distance, which is greater than zero, so that an associated object which is grasped by the forceps will not be damaged when said handles are squeezed, to a predetermined maximum distance upon a manipulation of said pair of handles; and,
a flange means, secured to one of said first and second body portions, for guiding an associated object in a controlled directional manner as one of said first and second jaws is retracted from the other of said first and second jaws, wherein said flange means comprises a planar flange which is substantially triangular in side elevational view and which extends approximately transversely to both said head portion and said arm, said flange being positioned near said arm.

15. The forceps of claim 14 wherein said second jaw includes:
a head portion;
a pair of spaced apart arms extending from a free end thereof; and,
a pair of fingers, one extending approximately transversely from each of said arms, said flange extending between said second jaw arms.

16. The forceps of claim 15 wherein said flange is so positioned that said first jaw arm and said second jar fingers release a centering strand of an associated intraocular lens in a controlled directional manner as said jaws are retracted from each other and as said centering strand is slid along said flange.

17. The forceps of claim 14 wherein said flange further includes a hook portion at a free end thereof, said hook portion being adapted to partially retract the iris or capsular flap of an eye during eye surgery as the forceps are used to insert an associated intraocular lens into said eye.

18. The forceps of claim 14 wherein said body first and second sections are curved with respect to one of said handles.

19. A surgical instrument for manipulating an intraocular lens of the type having centering strands during eye surgery, comprising:
a handle means for holding the instrument and including actuating means for manually actuating the instrument;
a body section operably connected to said handle means, said body section including a pair of integral jaw members which are axially slidable with respect to each other, said jaw members being adapted to grasp a centering strand of an associated intraocular lens; and,
a guide means for guiding the centering strand of said associated intraocular lens in a controlled directional manner as one of said jaws is retracted from the other of said jaws, said means being provided on said body section; and,
means for partially retracting the iris or capsular flap of an eye during the implantation of said intraocular lens in the eye, said means for partially retracting being provided on said body section.

20. The instrument of claim 19 wherein a first of said jaws includes a transversely extending arm portion and a second of said jaws also includes at least one transversely extending portion which is substantially parallel to said first jaw transversely extending arm portion.

21. The instrument of claim 19 wherein said guide means includes a flange which is substantially triangular in side elevational view, said flange having an angled surface and wherein said means for partially retracting includes a hook-shaped portion on a free end of said flange angled surface, said guide means also including a pair of spaced fingers of one of said jaw members, one of said pair of spaced fingers being positioned on either side of said flange so that the centering strand contacts said flange and said pair of fingers and is guided thereby as said fingers are moved in relation to said flange.

22. The instrument of claim 19 wherein said first and second jaw sections are slidable with respect to each other from a predetermined minimum distance, which is greater than zero so that a centering strand of an associated intraocular lens which is grasped by the forceps will not be damaged when the instrument is actuated, to a predetermined maximum distance.

23. A microsurgical instrument adapted for manipulating an intraocular lens of the type having centering strands, comprising:
a pair of resiliently biased handles;
a body section operably connected to said handles, said body section including a pair of integral jaw members extending at an angle to said body section, said jaw members being axially slidable with respect to each other and being adapted to grasp a centering strand of an associated intraocular lens; and, means for partially retracting the iris or capsular flap of an eye during the implantation of said associated intraocular lens in the eye, said means for partially retracting being provided on said body section adjacent one of said jaw members.

24. The instrument of claim 23 further comprising a means for releasing said centering strand of said associated intraocular lens in a controlled directional manner as one of said jaws is retracted from the other of said jaws.

25. The instrument of claim 24 wherein said means for releasing includes a flange having an angled surface and said means for partially retracting includes a hook-shaped portion provided at a free end of said flange, said flange being positioned on said body section and adjacent one of said jaw members.

26. The instrument of claim 24 wherein said first and second jaw sections are slidable with respect to each other from a predetermined minimum distance, which is greater than zero so that said centering strand of said associated intraocular lens will not be damaged when said handles are grasped, to a predetermined maximum distance.

27. The instrument of claim 23 wherein said body section is curved upwardly with respect to a longitudinal axis of at least one of said handles.

28. The instrument of claim 27 wherein said body section includes a first body member and a second body member which is substantially encircled by said first body member and wherein said second body member is slidable in relation to said first body member.

* * * * *